United States Patent [19]

Samsel

[11] Patent Number: 5,157,149

[45] Date of Patent: Oct. 20, 1992

[54] ENANTIOSELECTIVE SYNTHESIS OF L-(−)-4-BORONOPHENYLALANINE (L-BPA)

[75] Inventor: Edward G. Samsel, Baton Rouge, La.

[73] Assignee: The United States of America as represented by the United States Department of Energy, Washington, D.C.

[21] Appl. No.: 710,208

[22] Filed: Jun. 4, 1991

[51] Int. Cl.$^5$ ............................................. C07F 5/02
[52] U.S. Cl. ................................... 562/7; 260/665 G; 540/467; 549/455; 568/6
[58] Field of Search ................ 562/7; 549/455; 260/665 G; 540/467

[56] References Cited

U.S. PATENT DOCUMENTS

| | | |
|---|---|---|
| 2,898,365 | 8/1959 | Washburn et al. ............ 562/7 |
| 3,090,801 | 5/1963 | Washburn et al. ............ 562/7 |
| 4,483,853 | 11/1984 | Collins et al. ............... 562/7 |
| 4,499,082 | 2/1985 | Shenvi et al. ............... 562/7 |
| 4,613,460 | 9/1986 | Casati et al. ............... 560/41 |
| 4,939,288 | 7/1990 | Talley ...................... 560/81 |
| 4,994,607 | 2/1991 | Chan ....................... 562/496 |

FOREIGN PATENT DOCUMENTS

| | | | |
|---|---|---|---|
| 1040550 | 10/1958 | Fed. Rep. of Germany | 562/7 |
| 2104079 | 3/1983 | United Kingdom | 562/7 |

OTHER PUBLICATIONS

Snyder et al., *Chemical Abstracts*, vol. 52, No. 10923a (1958).

*Primary Examiner*—Jose G. Dees
*Assistant Examiner*—B. Frazier
*Attorney, Agent, or Firm*—James W. Weinberger; Thomas G. Anderson; William R. Moser

[57] ABSTRACT

A method of making substantially pure L-BPA is disclosed. The method includes the steps of reacting 4-bromobenzaldehyde with ethylene glycol to form 4-bromobenzaldehyde ethylene glycol acetal, sequentially reacting 4-bromobenzaldehyde ethyleneglycol acetal with Mg to produce the Grignard reagent and thereafter reacting with tributyl borate and then converting to an acid environment to form 4-boronobenzaldehyde, reacting 4-boronobenzaldehyde with diethanol amine to form 4-boronobenzaldehyde diethanolamine ester, condensing the 4-boronobenzaldehyde diethanolamine ester with 2-phenyl-2-oxazolin-5-one to form an azlactone, reacting the azlactone with an alkali metal hydroxide to form z-α-benzoylamino-4-boronocinnamic acid, asymmetrically hydrogenating the z-α-benzoylamino-4-boronocinnamic acid in the presence of a catalyst of a cheltate complex of rhodium (I) with chiral bisphosphines to form L-(+)-N-benzoyl-4-boronophenylalanine, and thereafter acidifying the L-(+)-N-benzoyl-4-boronophenylalanine in an organic medium to produce L-BPA.

24 Claims, 3 Drawing Sheets

ENANTIOSELECTIVE SYNTHESIS OF L-(−)-4-BORONOPHENYLALANINE (L-BPA)

CONTRACTUAL ORIGIN OF THE INVENTION

The U.S. Government has rights in this invention pursuant to Contract No. DE-AC07-76ID01570 the U.S. Department of Energy and Idaho National Engineering Laboratory (INEL).

BACKGROUND OF THE INVENTION

4-Boronophenylalanine (BPA) currently has Investigational New Drug (IND) status in the U.S.A. and is being extensively investigated in the U.S. and abroad for boron neutron capture therapy (BNCT) treatment of metastatic melanomas and other tumors. Its use to cure melanomas in Japan was reported in 1989. The rationale for its use is that BPA can be a mock biosynthetic precursor for melanin, which is normally made by the enzyme tyrosinase from dopa and tyrosine. It is widely believed that the pure enantiomer L-BPA, possessing S configuration, is more biologically active than is the D,L racemate.

The traditional synthetic route to D,L-BPA was developed by Snyder et al. in 1958 and reported in *Journal Am Chem. Soc.*, 1958, 80, 835. Pure L-BPA has been prepared by Kemp et al. in 1980 by resolving the racemic product of Snyder's synthesis. Thus, D,L-BPA was esterified and enantioselectively hydrolysed using the enzyme α-chymotrypsin. More recently, Glass et al. in 1983 have reported the selective hydrolysis of the N-acetamide derivative, Glass, J.; *Proc. First Intl. Symp. on Neutron Capture Therapy*, Cambridge, Mass. 1983. All methods of resolution suffer from the inherent disadvantage that, at most, only 50% of the racemic material can be recovered as a pure enantiomer; for BNCT purposes, at least 50% of the $^{10}$B isotope is discarded during resolution.

Accordingly, an object of the invention is the development of a direct enantioselective synthesis of L-BPA utilizing an asymmetric hydrogenation of prochiral olefins using chiral 1,2-diphosphine complexes of rhodium, such as those summarized in, *Asymmetric Synthesis*, Morrison, L. D., Ed.; Vol. 5; Academic Press: New York, 1985, the disclosure of which is herein incorporated. This technique was originally developed at Monsanto Corporation for the manufacture of L-DOPA, see U.S. Pat. Nos. 4,005,127, 4,142,992, 4,220,590 and others.

The catalysts used in this invention are chelate complexes of rhodium (I) with chiral bisphosphines. There are two general types of chiral bisphosphines known, shown in the diagram below. Both types possess phosphine groups linked by a two-carbon chain. In type 1, the center(s) of chirality, responsible for asymmetric induction in the catalytic hydrogenation reactions, lies in this two-carbon chain by virtue of its unsymmetrical substitution i.e. $R_1$ and/or $R_2 \neq H$. Type 1 bisphosphines are usually derived and prepared from naturally occurring optically active biochemicals, are commercially available and inexpensive. Type 1 includes the compounds trivially named Prophos, Chiraphos, Norphos, Diop and Binap. Type 2 bisphosphines possess an unsubstituted ethylene group linking two chiral phosphine groups, i.e. $R_3 \neq R_4$. Type 2 ligands were developed at Monsanto Corp. (U.S. Pat. No. 4,220,590) and are prepared synthetically and chemically resolved into enantiomers. The optimal bisphosphine of this type is trivially named Dipamp. In the present invention type 1 ligands are preferred due solely to their availability but type 2 bisphosphines are also effective.

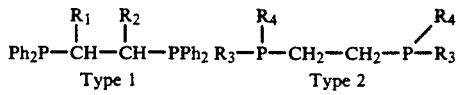

The active rhodium (I) catalyst is a cation which may be prepared in two ways. The first method is in-situ catalyst generation by combining appropriate amounts of bisphosphine and a suitable precursor rhodium complex such as [(diene)RhCl]$_2$, [(diene)Rh(acac)] (where diene may be 1,5-cyclooctadiene, norbornadiene or others and acac is acetonylacetone) or a cationic rhodium complex such as [(diene)$_2$Rh]X may be used (where X is a non-coordinating anion). These components are combined in a organic medium and the hydrogenation substrate is subsequently added, then hydrogen. The second method is prior isolation of the catalyst complex, [(bisphosphine) (diene)Rh]X, as described herein; combination of the substrate with this catalyst and addition of hydrogen allows hydrogenation to proceed, the substrate displacing diene from rhodium in the course of reaction. The second method is preferred for preparation scale reactions since superior yields and catalysts lifetimes occur. The first method is rapid and is preferred for screening the effectiveness of different bisphosphine ligands in asymmetric induction, although chemical yields are poor.

Those diphosphines which are readily available were examined for their ability to induce chirality in the reduction of the substrate of interest. The ligand called R-Prophos, originally developed by Bosnich, Fryzuk, M. D.; Bosnich, B.; *J. Am. Chem. Soc.*, 1979, 101, 3043; Fryzuk, M. D.; Bosnich, B.; *J. Am. Chem. Soc.*. 1977, 99, 6262, the disclosures of which are incorporated herein by reference, was found to be adequate for the preparation of L-BPA described below.

The use of cationic rhodium diphosphine complexes in catalytic hydrogenations is well established, but this is the first example in which a boronic acid group has been present on the olefin, and I have shown that it is well tolerated by the catalyst. The methodology described is adaptable to the synthesis of other α-amino acids containing this functionality. Moreover, the tolerance for this group suggests that other boron containing moieties, such as carboranes or closo-borane dianions could also be tolerated.

Another object of the invention is the method of making L-BPA comprising the steps of protecting 4-bromobenzaldehyde with ethylene glycol in the form of 4-bromobenzaldehyde ethylene glycol acetal, sequentially reacting 4-bromobenzaldehyde ethylene glycol acetal with Mg to produce the Grignard reagent and thereafter reacting with tributyl borate and then converting to an aqueous acid environment to form 4-boronobenzaldehyde, reacting 4-boronobenzaldehyde with diethanolamine to form 4-boronobenzaldehyde diethanolamine ester, condensing the 4-boronobenzaldehyde diethanolamine ester with 2-phenyl-2-oxazolin-5-one to form an azlactone, reacting the azlactone with an aqueous alkali metal hydroxide to form z-α-benzoylamino-4-boronocinnamic acid, asymmetrically hydrogenating the z-α-benzoylamino-4-boronocinnamic acid in the presence of a chiral diphosphine catalyst selected from the group including (consisting of) R-Prophos, Dipamp, Norphos, [(R)-1,2-bis (diphenylphosphinopropane)]rhodium(I) tetraflouroborate to form L-(+)-N-benzoyl-4-boronophenylalanine, and thereafter acidifying the L-(+)-N-benzoyl-4-boronophenylalanine in an organic medium to produce L-BPA.

Still another object of the invention is a method of making L-BPA comprising the steps of forming an ester of 4-boronobenzaldehyde, condensing the 4-boronobenzaldehyde ester with 2-phenyl-2-oxazolin-5-one to form an azlactone, reacting the azlactone with an alkali metal hydroxide to form z-α-benzoylamino-4-boronocinnamic acid, L asymmetrically hydrogenating the z-α-benzoylamino-4-boronocinnamic acid in the presence of a chiral diphosphine catalyst selected from the group including (consisting of) [(R)-1,2-bis (diphenylphosphinopropane)]rhodium(I) tetraflouroborate to form L-(+)-N-benzoyl-4-boronophenylalanine, and thereafter acidifying the L-(+)-N-benzoyl-4-boronophenylalanine in an organic medium to produce L-BPA.

A final object of the invention is a method of making L-BPA comprising the steps of asymmetrically hydrogenating z-α-benzoylamino-4-boronocinnamic acid in the presence of a chiral diphosphine catalyst selected from the group including (consisting of) R-Prophos, Dipamp, Norphos, [(R)-1,2-bis (diphenylphosphinopropane)]rhodium(I) tetraflouroborate to form L-(+)-N-benzoyl-4-boronophenylalanine, and thereafter acidifying the L-(+)-N-benzoyl-4-boronophenylalanine in an organic medium to produce L-BPA.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

DESCRIPTION OF THE PREFERRED EMBODIMENT

Figure 1A:
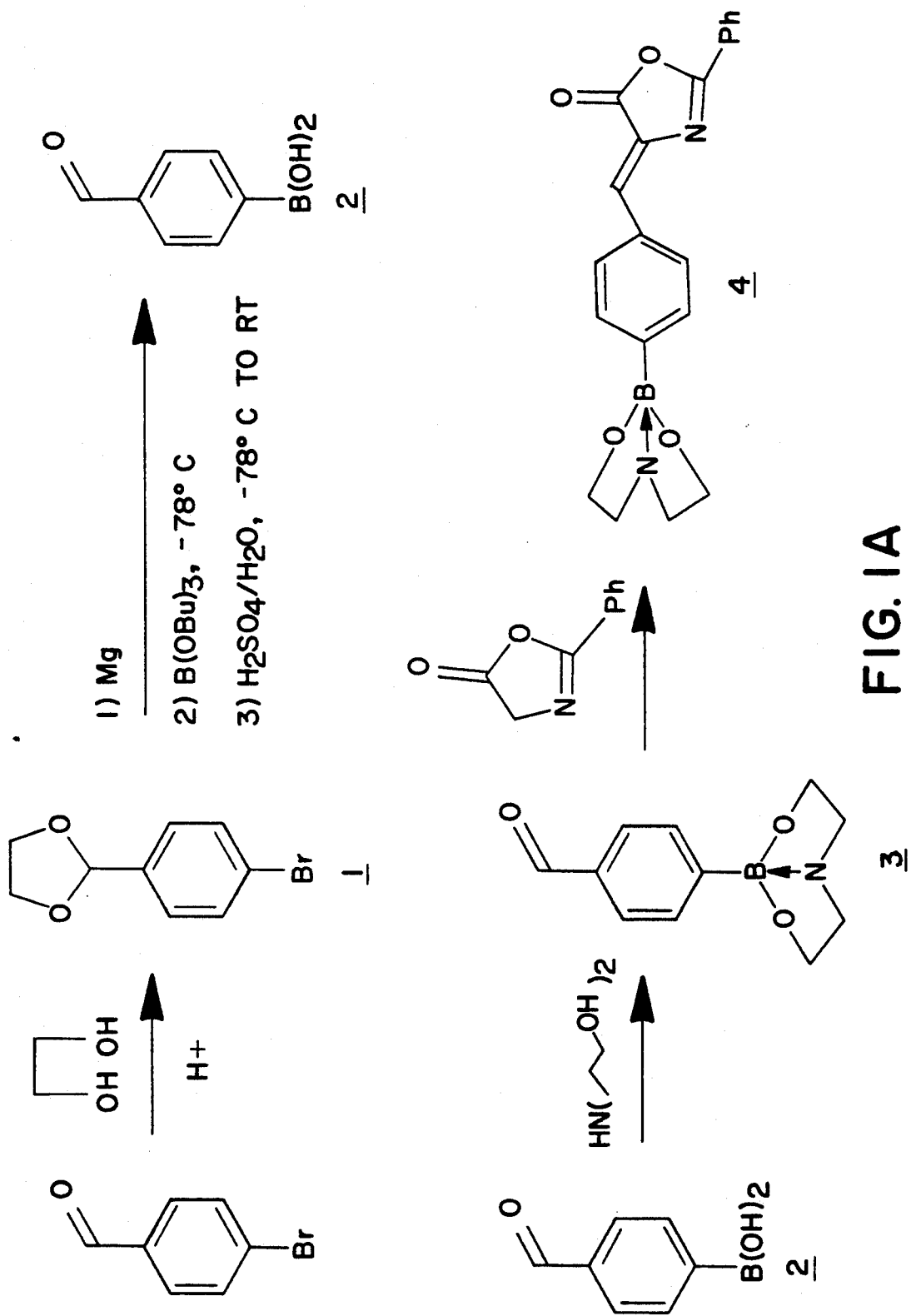
FIG. 1 is a series of chemical equations illustrating the invention.
Figure 1B:
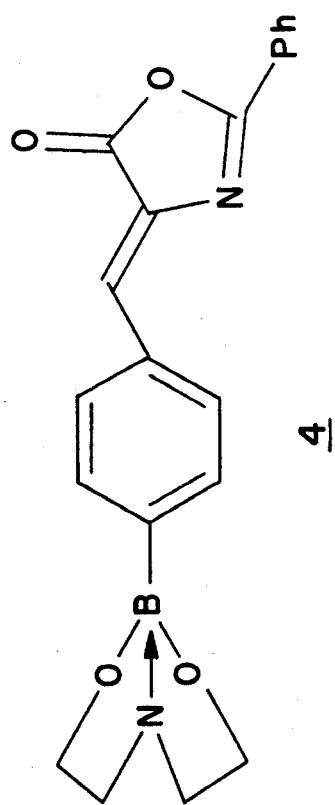
Figure 1B:
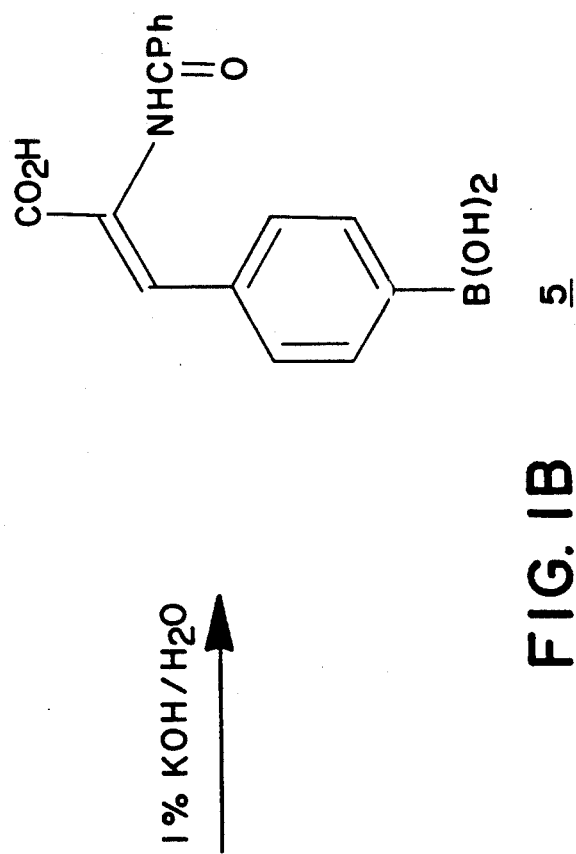
Figure 1C:
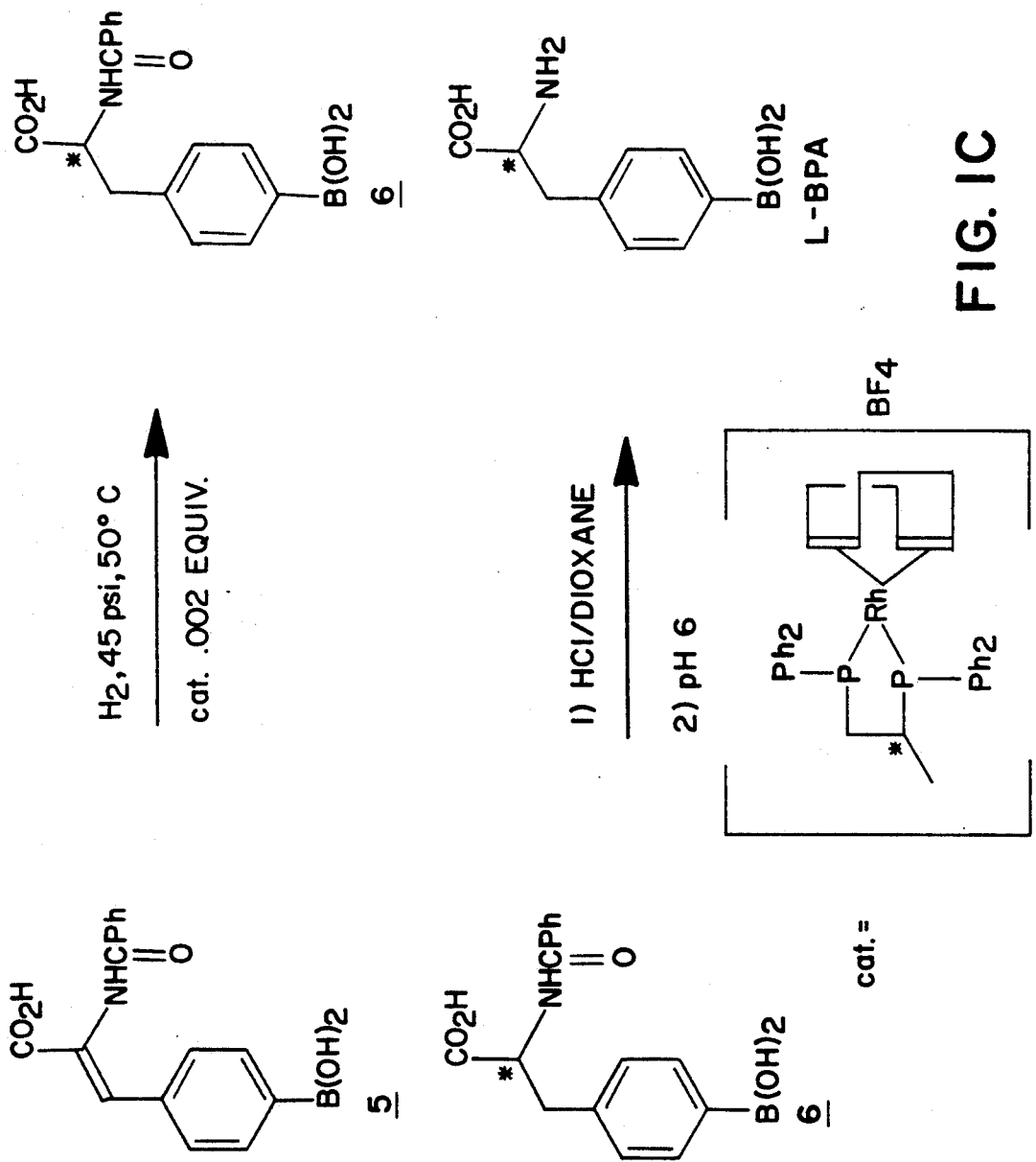

The methods of the invention are outlined in the following preparation scheme. All compounds were characterized by high-field NMR ($^1$H, $^{13}$C, $^{11}$B) and by IR; new compounds were also characterized by combustion analysis (C,H,N). Bracketed numerals refer to like numbered reactions or reaction products in the drawing of the specification. In the first step 4-boronobenzaledhyde (2) was prepared in 93% yield from the ethylene glycol acetal of 4-bromobenzaldehyde (1) by a Grignard reaction with tributyl borate ($^{10}$B enriched material may be used). The hydrolysis must be done at low temperature to produce (2) in high efficiency. Direct reaction of aldehyde (2) with uric or hippuric acid by the conventional procedure is not possible, as all attempts resulted in B-C cleavage. Therefore, the boronic acid group was protected by esterification with diethanolamine giving compound (3). Since the B-C cleavage described above probably resulted from reaction of the aryl boronic acid and ester with acetic anhydride, 2-phenyl-2-oxazolin-5-one was prepared and achieved the preparation of azlactone (4) in 62% yield by refluxing in dioxane. Boiling yellow (4) in 1% KOH.H$_2$O for 15 min produced a colorless solution which, upon acidification, precipitated white N-benzoylamino-4-boronocinnamic acid (5) in 87% yield. The product was the desired Z isomer as evidenced by its vinyl resonance at δ7.44; the undesirable E isomer should resonate a δ6.66, by analogy with its unboronated analogue, but no E isomer was observed.

The ability of the various chiral diphosphines to induce asymmetry in the hydrogenation of (5) was not previously known nor was the stability of the catalyst to the boronic acid group known. An in situ screening method was devised to evaluate the effectiveness of the phosphines and the configuration of their products. The optical rotations were measured and are shown in Table 1.

TABLE 1

| Chiral Diphosphine Screening[1] | | |
|---|---|---|
| Trivial Name | Supplier | $[\alpha]_{23}^D$ |
| (R)-Prophos | Strem | +50° |
| (S,S)-BDPP | Strem | −40° |
| (S,S)-Diop | Aldrich | −23° |
| (S)-Binap | Aldrich | −19° |

The specific rotation of optically pure (6) is not known but the measured values are indicative of relative effectiveness. Subsequent hydrolysis of the product (6) formed with R-Prophos was shown to be L-BPA by comparison with authentic material, so that the sign of the rotation of (6) bearing the S configuration is (+). Of the phosphines tested, only R-Prophos gives (+), and this ligand also produced the highest optical yield of either configuration. The most significant aspect of this screening is that the results in the table closely parallel the results reported in Koenig, K. E. which refers to *Asymmetric Synthesis*, p.p. 71–103, for hydrogenation of N-benzoylamidocinnamic acid without a boronic acid substituent. The catalyst is insensitive to the presence of this group in the para position. Therefore, those phosphines which are known to be superior to R-Prophos (e.g. DIPAMP, Norphos) may be used to good effect in this reaction.

Preparative hydrogenations were conducted with the preformed (1,5-COD) (Prophos) Rh(I) cationic complex shown in the scheme. This type of catalyst was developed by Schrock (Schrock, R. R.; Osborn, J. A.; *J. Am. Chem. Soc.* 1976, 98, 2134; ibid., 1971, 93, 2397) and is readily prepared from [(1,5-COD)RhC)]$_2$ or its norbornadiene analogue, Abel, E. W.; Bennett, B. A.; Wilkinson, G.; *J. Chem. Soc.* 1959, 3178. The hydrogenations proceed at 45 psi and 50° C. in excellent chemical yield.

The optical yield of the hydrogenation reactions depend on the ratio of catalyst to substrate. For example, the use of 1/500 equivalents produced L-(+)-6 with 88% enantiomeric excess (e.e.), while the use of 1/1000 equivalents of catalyst gave product with only 76% e.e. These values of e.e. were determined for L-BPA, obtained by hydrolysis of the hydrogenation products (6) and before crystallization of the L-BPA; the method used was developed at INEL and involves chiral HPLC analysis. Measurement of e.e. values by polarimetry is precluded by the unknown specific rotation of optically pure (6) and by the low specific rotation of LBPA.

Although optical yields were less than 90%, enantiomerically pure L-BPA was readily isolated by crystallizing the product of the hydrolysis of (6). During crystallization the crude L-BPA resolved itself to give product with greater than 96% e.e. and enantiomerically impure mother liquor. The isolated yield of pure L-BPA was 67%.

The procedures described here constitute the first practical route for the bulk preparation of pure L-BPA. The product is prepared in 23% overall yield from 4-bromobenzaldehyde as opposed to less than 5% overall yield from 4-bromotoluene by the conventional method of enzymatic hydrolysis of BPA-ethyl ester. The high cost of rhodium is offset by its high catalytic efficiency, and the rhodium can be recovered and recycled by conventional methods. A specific example of preparation is set forth.

Solvents were reagent grade and used as received from their commercial source unless otherwise noted. Reactions were conducted under air except as noted below.

The Nuclear Magnetic Resonance (NMR) used was a Bruker AC-P-300 broadband instrument operating at 300 MHz for $^1H$, 75.5 MHz for $^{13}C$ and 96.3 MHz for $^{11}B$. Chemical shifts in $^2H$ and $^{13}C$ spectra are referenced to the solvent resonances except for aqueous solutions where 3-(trimethylsilyl) tetradeuterio proprionic acid sodium salt ($\delta 0$) is used as an internal standard. Coupling constants (J) are in Hz. Chemical shifts in $^{11}B$ spectra are references to external $BF_3.Et_2O$ which was used in a coaxial capillary tube. IR spectra were recorded on a Perkin-Elmer 1420 spectrophotometer. Polarimetry was conducted on a Carl Zeiss Polarimeter, read to the nearest 0.01°, using a NaD lamp and filter with a 4 dm cell. Determination of the enantiomeric excess (% ee) in L-BPA was by a High Performance Liquid Chromatography (HPLC) method developed at INEL by Dr. W. F. Bauer utilizing ligand exchange chromatography with a $CuOAc_2$-L-proline chiral mobile phase and a C-18 reverse phase column. Elemental combustion analyses were conducted at INEL using a Carlo Erba EA1108 elemental analyzer.

4-Bromobenzaldehyde ethyleneglycol acetal (1)

A 250 mL round bottom flask, fitted with a stirbar, a Dean-Stark trap, condenser and attached to a vacuum-/argon dual manifold, was charged with 100 mL of toluene, 0.5 g of p-toluenylsulfonic acid hydrate, 18 mL of ethyleneglycol and 50.0 g (0.270 mol) of 4-bromobenzaldehyde (Aldrich); the trap was charged with 60 mL toluene. The apparatus was briefly degassed by evacuation and filled with Ar, then refluxed for 5 hr. during which 6.6 mL of $H_2O$ was collected. The solution was stirred with 10 g anhydrous $Na_2CO_3$, filtered and rotary evaporated. The residue was fractionally vacuum distilled through a 12 cm jacketed vigreux column, discarding a small forerun, and the product (BP 80°-85° C., 0.1 mm) was collected directly in a tared Schlenk flask, 60.1 g (0.26 mol, 97%). The product can crystallize on standing (mp 28°-32°) but is generally used as a neat liquid. $^1H$ NMR ($CDCl_3$): 7.50 (d, J=8.2, 2H), 7.34 (d, J=8.2, 2H), 5.75 (s,1H), 4.1-3.9 (m, 4H). $\{^1H\}^{13}C$ ($CDCl_3$): 136.98, 131.41, 128.13, 123.14, 102.94, 65.23.

4-boronobenzaldehyde (2)

All glassware used in the Grignard reaction was oven dried at 150°, assembled while hot, evacuated and filled with Ar. THF used was distilled from Na-benzophenone under $N_2$ using syringe techniques.

A 1 L 3-neck round bottom flask was fitted with a glass stirring shaft, bushing adapter and teflon blade, with a 250 mL pressure-equalized dropping funnel and septum, and a vacuum/Ar adapter attached to a Schlenk dual manifold. This was charged with 5.99 g (0.246 mol) of Mg turnings (Aldrich), evacuated, flame dried and placed under Ar before adding 300 mL of THF. 4-Bromobenzaldehyde ethylene glycol acetal (60.1 g, 0.262 mol) was dissolved in 50 mL of THF and added to the dropping funnel with a cannula. A small amount of the aryl bromide and a crystal of $I_2$ was added to the flask at 22° C. to initiate the reaction, thereafter the bromide was added slowly at 0° C. over 2.5 h and the mixture was stirred an additional 1 h at room temperature until the Mg was nearly all consumed. The solution was then cooled to −80° C. at which temperature it solidifies and was kept semisolid by agitation with the stirrer. Tributylborate (73 mL, 0.271 mol, Aldrich) was added to the funnel with a cannula and run into the flask over 5 min; at this stage $^{10}B$ enriched tributyl borate can be substituted. The mixture was warmed to 0° C. with melting and stirred 15 min. before cooling again to −80° C. where it remains liquid. In a separate Schlenk flask, 125 mL of 10% $H_2SO_4$ was degassed and placed under Ar before transfer to the dropping funnel with a cannula. This was added to the cold solution over 10 min. to give a yellow slurry, which was warmed to 22° C. with stirring. In air, 100 mL of 50% aq. tetrahydrofuran (THF) was added and the slurry was poured into a 2 L round bottom flask and most of the THF was removed by rotary evaporation. Ether (500 mL) and $H_2O$ (100 mL) were added and the solution was transferred to a separatory funnel (any solids which separate should be carried with the organic phase). The phases were separated and the $Et_2O$ was washed with 100 mL $H_2O$, 50 mL brine then dried with 50 g anhydrous $Na_2SO_4$. After filtration, the $Et_2O$ was removed by rotary evaporation and, to facilitate removal of alcohols, 100 mL THF and 25 mL $H_2O$ were twice added and evaporated (22 mmHg, bath temperature 40° C.).

The resulting solid was recrystallized from the minimum amount (ca. 130 mL) of boiling 5% aq. THF, completing the crystallization by the addition of 250 mL of hexanes, in portions, at −4° C., giving 29.7 g. (0.198 mol, 81%) of 4-boronobenzaldehyde. From the mother liquor was recovered, by crystallization from THF with hexanes, another 4.6 g, total yield 34.3 g (0.229 mol, 93%). The first crop was analytically pure but all was used in subsequent steps. $^1H$ NMR ($Me_2CO$-$d_6$): $\delta 10.07$ (s, 1H), 8.05 (d, 2H J-8.1 Hz), 7.89 (d, 2H, 8.1 Hz), 7.48 (s, 2H). $\{^1H\}^{13}C$: $\delta 193\ 03$, 138.56, 135.17, 128.89, 129.08. $\{^1H\}^{11}B$: $\delta 29.1$ (s, 159 Hz width). IR(-CsI): 1670 cm$^{-1}$(br, $\nu co$) Anal. Calcd for $C_7H_7BO_3$: C, 56.07; H, 4.71. Found: C, 56.45, H 4.94.

4-boronobenzaldehyde diethanolamine ester (3)

A solution of diethanolamine (25.75 g, 0.245 mol, Fisher) in 275 mL THF was stirred into a solution of 4-boronobenzaldehyde (34.0 g, .0.227 mol) in 500 mL THF at room temperature, inducing precipitation of white solid. The mixture was stirred at room temperature 5 min., allowed to stand 1 h, then stored at −4° C. overnight.

The product was filtered, washed with 100 mL hexanes and dried in vacuo (35.2 g, 0.161 mol, 71%). The mother liquor was rotary evaporated, and the residue taken up in 75 mL of THF; standing at −4° C. overnight afforded an additional 2.3 g (total yield 37.5 g, 0.171 mol, 75.5% based on Mg). $^1$H NMR (Me$_2$SO-d$_6$): δ9.94 (s, 1H), 7.73 (d, 2H, J=8.1 Hz), 7.65 (d, 2H, J=8.1 Hz), 7.03(br s, 1H, NH), 3.92-3.76 (m, 4H), 3.1 (m, 2H), 2.9 (m, 2H). {$^1$H}$^{13}$C (Me$_2$SO-d$_6$): δ193.4, 135.0, 133.2, 127.9, 63.1, 50.8. {$^1$H}$^{11}$B (Me$_2$SO-d$_6$): δ10.35 (s, 272 Hz width) IR (CsI): 1701 cm$^{-1}$ (νCO) Anal. Calcd for C$_{11}$H$_{14}$BNO$_3$: C, 60.32; H, 6.44. Found: C, 60.37, H, 6.67.

2-Phenyl-2-oxazolin-5-one

This procedure is a modification of Crawford and Little (J. Chem. Soc. 1959, 729). A flask containing hippuric acid (20 g, 0.011 mol, Aldrich) and acetic anhydride (130 mL) was placed in a boiling H$_2$O bath (90° C.) and vigorously stirred for exactly 15 min. The solution was poured onto 200 mL of toluene, 200 mL of ice water and stirred vigorously for 5 min. The phases were separated and the organic phase was stirred with 1 L of 2% aq. NaHCO$_3$ for 10 min., separated and dried with anhydrous Na$_2$SO$_4$. Filtration of the solution and rotary evaporation (bath temperature 35° C., 20 mmHg) gave a yellow white solid. The formation of a red material in this procedure is due to protect degradation and condensation. Yield 11.8 g, 66%, mp 83°–86°. $^1$H NMR (CDCl$_3$): δ7.95 (d, 2H; J=7 Hz); 7.55 (t, 1H, J=7 Hz), 7.45 (t, 2H, J=7 Hz), 4.38 (s, 1H). $^{13}$C NMR (CDCl$_3$): 175.9, 163.4, 132.7, 128.8, 127.7, 125.8, 54.9.

Azlactone (4)

4-Boronobenzaldehyde diethanolamine ester (3) undergoes Perkin-Erlenmeyer condensation with 2-phenyl-2-oxazolin-5-one in the following procedure. The aldehyde (37.0 g, 0.169 mol) and the oxazolinone (37 g, 0.23 mol) were dissolved in L of 1 1,4-dioxane in a round bottom flask, and the solution was refluxed for 3 h giving the z-azlactone product as a yellow precipitate. The slurry was cooled to room temperature, stirred 10 min. with 1 L Et$_2$O, filtered, washed with 0.5 L Et O and dried in vacuo (yield 37.8 g, .0.104 mol, 62%) $^1$H NMR (Me$_2$SO-d$_6$): δ8.13 (m, 4H), 7.75-7.59 (m, 5H), 7.32 (s, 1H, vinyl), 7.01 (br, s, NH), 3.95-3.79 (m, 4H), 3.13 (m, 2H), 2.89 (m, 2H). {$^1$H}$^{13}$C (Me$_2$SO-d$_6$): δ167.1, 162.2, 133.45, 133.18, 132.34, 131.75, 131.53, 130.89, 129.32, 127.87, 127.79, 125.25, 63.0, 50.7 {$^1$H}$^{11}$B (Me$_2$SO-d$_6$): δ10.8 (s, width 470 Hz). IR (Nujol, cm$^{-1}$): 1775, 1755, 1640, 1595. Anal. calcd for C$_{20}$H$_{19}$BN$_2$O$_4$: C, 66.32; H, 5.29; N, 7.73. Found: C, 66.26; H, 5.48; N, 7.64.

Z-α-Benzoylamino-4-boronocinnamic acid (5)

Azlactone 4 (37.5 g, 0.104 mmol) was added to a beaker with 1.9 L (0.29 mol) of boiling 1% KOH-H$_2$O, and boiled with vigorous stirring until the solution was nearly colorless and homogeneous (15 min). The solution was cooled, filtered to remove a small amount of white solid, neutralized and adjusted to pH 3 with conc. HCl. The white precipitate was filtered, washed thoroughly with water and dried in vacuo (yield 28.0 g, 0.090 mol, 87%). $^1$H NMR (Me$_2$SO-d$_6$): δ12.7 (v. br. s, 1H); 9.97 (s, 1H); 8.12 (s, 2H, HOB): 7.98 ( δ, J=7.56 Hz, 2H); 7.78 (d, J=7.02 Hz, 2H); 7.61 (d, J=7.56 Hz, 2H); 7.53 (m, 3H), 7.44 (s, $^1$H, vinyl). {$^1$H}$^{13}$C (Me$_2$SO-d$_6$): δ166.39, 166. 08; 135.49, 135.27, 134.24, 133.62, 133.07, 131.86, 128.72, 128.55, 127.80, 127.71. {$^1$H}$^{11}$B(Me$_2$SO): δ29 (s, 1200 Hz width). IR (CsI, cm$^{-1}$): 1712, 1660, 1605, 1583. Anal. calcd for C$_{16}$H$_{14}$BNO$_5$: C, 61.77; H, 4.54; N, 4.50 Found: C, 61.30; H, 4.70; N, 4,47. Synthesis of [1,5-cyclooctadienyl)(R-1,2-bis (diphenylphosphinopropane)Rhodium (I)]tetraflouroborate This catalyst is prepared as described below. A 50 ml solution of 90% aqueous methanol was degassed in vacuo and purged with Ar (×3). (Chloro) (1,5 cyclooctadienyl) Rh(I) dimer (Alfa) (0.50 g, 1.02 mmol) and R-Prophos (Strem) (0.82 g, 2.02 mmol) were combined in a 25 ml Schlenk flask. This flask was evacuated and filled with Ar (×3). The methanol solution (8 mL) was added and the mixture was stirred in a 40°–45° C. water bath for 2 h. A light precipitate was present. Additional methanol solution (5 mL) was added and the reaction stirred for 0.5 h. The reaction mixture was Schlenk filtered. NaBF$_4$ (11.2 g, 102 mmol) was dissolved in 100 mL distilled water. This solution was degassed and added to the reaction solution dropwise via syringe. Yellow precipitate formed. The precipitate was filtered, washed with water and dried in vacuo. The final product (1.27 g, 1.96 mmol) was recovered in 97% yield.

General Asymmetric Hydrogenation Procedure

The procedure for the asymmetric hydrogenations is a modification of that of Knowles, W. S.; Vineyard, B. D.; Sabacky, M. J.; Bachman, G. L.; Weinkauf, D. J. J. Am Chem. Soc. 1977, 99, 5946, the disclosure of which is incorporated by reference. Hydrogenations were conducted in Fischer-Porter pressure bottles (Aerosol Laboratory Equipment Corp.) fitted with pressure heads which have been described J. Am.Chem.Soc. 1981, 103, 7520), (Murray, Samsel et al., attached through swagelok fittings and tubing to a regulated H$_2$ bottle. The bottles were charged with a stir-bar, 10–18 g of substrate (5) catalyst (1/500 to 1/800 equiv.) and MeOH (14 to 20 mL/g substrate). The bottles were attached to the pressure head and the swagelok fitting on the ball-valve was connected to a vacuum Ar dual manifold. With magnetic stirring, the bottle was evacuated and filled with Ar three times, then evacuated and filled with H$_2$ to 45 psi. It was then placed in a thermostated oil bath and stirred at this pressure at 50°–55° C. for 3–20 h or until Hz uptake ceased. The product was then isolated as described in the typical example given below.

L-(+)-N-Benzoyl-4-boronophenylalanine (6)

Substrate (5) (10.0 g, 32.1 mmol), catalyst (41.6 mg, 0.064 mmol) and MeOH (250 mL, Fisher HPLC grade) were placed in a 500 mL Fischer-Porter bottle and hydrogenated 5 h. The solvent was rotary evaporated and the residue was taken up in 350 mL of 0.2N KOH, filtered through a medium frit to remove catalyst residues, and acidified to pH 2 with conc. HCl. The precipitated product was filtered, washed with H$_2$O and dried in vacuo to give 6 (9.53 g, 30.4 mmol, 95%). $^1$H NMR (Me$_2$SO-d$_6$): δ12.77 (br. s, 1H); 8.70 (d, 1H, J=8.1); 7.94 (s, 2H); 7.79 (d, 2H, J=7.0); 7.67 (d, 2H, J=7.6); 7.45 (m, 3H); 7.27 (d, 2H, J=8.1); 4.63 (m, 1H); 3.13 (m, 2H). {$^1$H}$^{13}$C (Me$_2$SO-d$_6$): δ173.1, 166.3 140.1, 134.04, 133.90, 131.96 (br), 131.36, 128.24, 128.12, 127.32. {$^1$H}$^{11}$B (Me$_2$SO-d$_6$): δ27 (1500 Hz width). IR (Cs I, cm$^{-1}$): 1736, 1654, 1542, 1371. Anal. calcd for $C_{16}H_{16}BNO_5$: C, 61.37; H, 5.15; N, 4.47. Found: C, 61.51; H, 5.11; N, 4.47.

L-(−)-4-boronophenylalanine (L-BPA)

The benzoyl derivative (6) (9.53 g, 30.4 mmol), 195 mL of 5N HCl and 95 mL of 1,4-dioxane were placed in a 500 mL round bottom flask fitted with a condenser, adapter and attached to a Schlenk dual manifold. The mixture was thoroughly degassed by evacuating and filling with Ar three times, then the mixture was refluxed under Ar for 24 h. The flask was opened and the contents rotary evaporated. To remove gross amounts of HCl 50 mL $H_2O$ was twice added and evaporated. The mixture was then slurried with 50 mL of 0.2N HCl, filtered, and the benzoic acid washed with 2×50 mL of 0.2N HCl. The filtrate was neutralized to pH 6-6.5 with 3N KOH, and was stored at +4° C. 12 h to complete crystallization. The product was filtered, washed with $H_2O$ and dried in vacuo (4.25 g, 20.3 mmol, 67%). Analysis by chiral HPLC indicated the ratio of L to D isomers to be ca. 63 to 1 (>96% ee), while analysis of an aliquot of the crude HCl salt taken before neutralization indicated 89% ee. The mother liquor from the above filtration was evaporated to 30 mL, cooled, and the resulting crop was filtered, washed and dried (0.50 g); this was not combined, as HPLC analysis indicated the ratio of L to D isomers to be 0.47. NMR analysis was conducted in $D_2O$ containing a trace of conc. HCl for solubility but this medium scrambles the boronic acid protons. The data are identical to that obtained with commercially supplied L-BPA (Callery Chemical). $^1H$ NMR ($D_2O$-HCl): δ7.77 (d, J=7.47, 2H); 7.37 (d, J=7.47, 2H) 4.41 (approx t, J=6.5, 1H), 3.3 (m, 2H). $\{^1H\}^{13}C$ NMR: 174.1, 139.66, 137.36, 132.38, 131.95, 56.8, 38.5. $\{^1H\}^{11}B$: δ29.0 (600 Hz Width).

While there has been disclosed what is considered to be the preferred embodiment of the present invention, it is understood that various changes in the details may be made without departing from the spirit, or sacrificing any of the advantages of the present invention.

The embodiments of the invention in which an exclusive property or privilege is claimed are defined as follows:

1. A method of making L-BPA comprising the steps of reacting 4-bromobenzaldehyde with ethylene glycol to form 4-bromobenzaldehyde ethylene glycol acetal, sequentially reacting 4-bromobenzaldehyde ethyleneglycol acetal with Mg to produce the Grignard reagent and thereafter reacting with tributyl borate and then converting to an acid environment to form 4-boronobenzaldehyde, reacting 4-boronobenzaldehyde with diethanolamine to form 4-boronobenzaldehyde diethanolamine ester, condensing the 4-boronobenzaldehyde diethanolamine ester with 2-phenyl-2-oxazolin-5-one to form azlactone, reacting the azlactone with an alkali metal hydroxide to form z-α-benzoylamino-4-boronocinnamic acid, asymmetrically hydrogenating the z-α-benzoylamino-4-boronocinnamic acid in the presence of a catalyst of a chelate complex of rhodium (I) with chiral bisphosphines to form L-(+)-N-benzoyl-4-boronophenylalanine, and thereafter acidifying the L-(+)-N-benzoyl-4-boronophenylalanine in an organic medium to produce L-BPA.

2. The method of claim 1, wherein the L-BPA is substantially pure.

3. The method of claim 1, wherein the overall yield of L-BPA exceeds 20%.

4. The method of claim 1, wherein the 4-bromobenzaldehyde ethylene glycol acetal is dissolved in tetrahydrofuran to which is added arylbromide with a crystal of $I_2$ as an initiator to initiate the reaction at about 22° C. and thereafter Mg metal is added and the mixture agitated for a time sufficient to dissolve the Mg.

5. The method of claim 4, wherein the reaction mixture is cooled to about −80° C. and the tributylborate is added and thereafter sulfuric acid is added and the solution is heated to ambient temperatures whereupon solid 4-boronobenzaldehyde is separated.

6. The method of claim 1, wherein the reaction of 4-boronobenzaldehyde with diethanolamine is at ambient temperature.

7. The method of claim 1, wherein the azlactone is produced by refluxing 4-boronobenzaldehyde diethanolamine ester and 2-phenyl-2-oxazolin-5-one for about three hours at an elevated temperature followed by cooling to room temperature and filtering and washing with a suitable organic material.

8. The method of claim 1, wherein azlactone is boiled with dilute KOH and agitated and thereafter cooled and filtered to produce 2-α-benzylamino-4-boronocinnamic acid.

9. The method of claim 1, wherein the asymmetric hydrogenation of z-α-benzoylamino-4-boronocinnamic acid takes place at elevated temperature and pressure.

10. The method of claim 9, wherein the elevated pressure is about 45 psi and the elevated temperature is about 50° C.

11. The method of claim 1, where the L-(+)-N-benzoyl-4-boronophenylalanine is acidified with a mineral acid.

12. The method of claim 11, wherein the mineral acid is HCl.

13. The method of claim 1, wherein the catalyst is selected from the group consisting of catalyst selected from R-Prophos, Dipamp, Norphos, [(R)-1,2-bis (diphenylphosphinopropane)]rhodium(I) tetraflouroborate.

14. A method of making L-BPA comprising the steps of, forming an ester of 4-boronobenzaldehyde, condensing the 4-boronobenzaldehyde ester with 2-phenyl-2-oxazolin-5-one to form azlactone, reacting the azlactone with an alkali metal hydroxide to form z-α-benzoylamino-4-boronocinnamic acid, asymmetrically hydrogenating the z-α-benzoylamino-4-boronocinnamic acid in the presence of a catalyst of a chelate complex of rhodium (I) with chiral bisphosphines to form L-(+)-N-benzoyl-4-boronophenylalanine, and thereafter acidifying the L-(+)-N-benzoyl-4-boronophenylalanine in an organic medium to produce L-BPA.

15. The method of claim 1, wherein the L-BPA is more than 95% pure.

16. The method of claim 14, wherein the overall yield of L-BPA exceeds 20%.

17. The method of claim 14, wherein the 4-bromobenzaldehyde ethylene glycol acetal is dissolved in tetrahydrofuran to which is added arylbromide with a crystal of $I_2$ as an initiator to initiate the reaction at about 22° C. and thereafter Mg metal is added and the mixture agitated for a time sufficient to dissolve the Mg.

18. The method of claim 17, wherein the reaction mixture is cooled to about −80° and the tributylborate is added and thereafter sulfuric acid is added and the solution is heated to ambient temperatures whereupon solid 4-boronobenzaldehyde is separated.

19. The method of claim 14, wherein the azlactone is produced by refluxing 4-boronobenzaldehyde diethanolamine ester and 2-phenyl-2-oxazolin-5-one for about three hours at an elevated temperature followed by cooling to room temperature and filtering and washing with a suitable organic material.

20. The method of claim 14, wherein azlactone is boiled with dilute KOH and agitated and thereafter cooled and filtered to produce 2-α-benzylamino-4-boronocinnamic acid.

21. The method of claim 14, wherein the asymmetric hydrogenation of z-α-benzoylamino-4-boronocinnamic acid takes place at elevated temperature and pressure.

22. The method of claim 14, wherein the catalyst is selected from the group consisting of chiral diphosphine catalyst selected from R-Prophos, Dipamp, Norphos, R-Prophos, Dipamp, Norphos, [(R)-1,2-bis (diphenylphosphinopropane)]rhodium(I) tetraflouroborate.

23. The method of claim 14, wherein the azlactone is produced by refluxing 4-boronobenzaldehyde diethanolamine ester and 2-phenyl-2-oxazolin-5-one for about three hours at an elevated temperature followed by cooling to room temperature and filtering and washing with a suitable organic material.

24. The method of claim 14, wherein azlactone is boiled with dilute KOH and agitated and thereafter cooled and filtered to produce 2-α-benzylamino-4-boronocinnamic acid.

* * * * *